(12) United States Patent
Palazzo et al.

(10) Patent No.: US 11,209,408 B2
(45) Date of Patent: Dec. 28, 2021

(54) COOKING OIL PUMPING STATION WITH OIL QUALITY SENSOR

(71) Applicant: Frontline International, Inc., Cuyahoga Falls, OH (US)

(72) Inventors: John W. Palazzo, Akron, OH (US); Giovanni Brienza, Copley, OH (US)

(73) Assignee: FRONTLINE INTERNATIONAL, INC., Cuyahoga Falls, OH (US)

( * ) Notice: Subject to any disclaimer, the term of this patent is extended or adjusted under 35 U.S.C. 154(b) by 0 days.

(21) Appl. No.: 16/358,605

(22) Filed: Mar. 19, 2019

(65) Prior Publication Data

US 2020/0300831 A1    Sep. 24, 2020

(51) Int. Cl.
| | |
|---|---|
| *G01N 33/03* | (2006.01) |
| *A47J 37/12* | (2006.01) |
| *A23L 5/10* | (2016.01) |
| *G01N 1/14* | (2006.01) |

(52) U.S. Cl.
CPC ................ *G01N 33/03* (2013.01); *A23L 5/11* (2016.08); *A47J 37/1266* (2013.01); *A47J 37/1271* (2013.01); *G01N 1/14* (2013.01); *A23V 2002/00* (2013.01)

(58) Field of Classification Search
CPC ....... G01N 33/03; G01N 1/14; A47J 37/1266; A47J 37/1271; A23L 5/11
See application file for complete search history.

(56) References Cited

U.S. PATENT DOCUMENTS

| | | | |
|---|---|---|---|
| 8,497,691 | B2 | 7/2013 | Behle et al. |
| 9,861,233 | B2 | 1/2018 | McGhee et al. |
| 2004/0000543 | A1* | 1/2004 | Dudek ..................... A21B 2/00 |
| | | | 219/655 |
| 2009/0153155 | A1 | 6/2009 | Chambon et al. |
| 2015/0374173 | A1 | 12/2015 | McGhee et al. |
| 2016/0033463 | A1 | 2/2016 | Robertson et al. |
| 2016/0109887 | A1 | 4/2016 | Palazzo et al. |
| 2017/0030880 | A1 | 2/2017 | Behle et al. |
| 2017/0176369 | A1* | 6/2017 | Lambert ................ G01N 27/12 |
| 2017/0367535 | A1* | 12/2017 | Gotz .................... G01N 27/221 |

FOREIGN PATENT DOCUMENTS

| | | |
|---|---|---|
| WO | 2010/148133 A1 | 12/2010 |
| WO | 2017/087361 A1 | 5/2017 |

* cited by examiner

*Primary Examiner* — Anthony J Weier
(74) *Attorney, Agent, or Firm* — Emerson, Thomson & Bennett, LLC; Roger D. Emerson

(57) ABSTRACT

A system for transporting and measuring the quality of cooking oil in a system. The system may include a fryer unit, a feed tank, a storage receptacle, and either a pumping station, direct flow pathway from the fryer unit to the storage receptacle, or both a pumping station and a direct flow pathway from the fryer unit to the storage receptacle. At least one oil quality sensor for measuring the quality of the oil, such as by measuring the electrical properties of the oil, may be placed in one of the various lines of the pumping station, in the direct flow pathway from the fryer unit to the storage receptacle, or any combination thereof.

9 Claims, 12 Drawing Sheets

COOKING OIL PUMPING STATION WITH OIL QUALITY SENSOR

TECHNICAL FIELD

The present invention relates generally to an apparatus for disposing of cooking oil. More particularly, the present invention relates to the removal and disposal of spent cooking oil, or waste oil, from a fryer. Specifically, the present invention relates to measuring the quality of oil exiting a fryer vat, either by routing cooking oil directly from a fryer vat to a storage receptacle, or alternatively by routing oil through a pumping station located external to the fryer unit.

BACKGROUND

Most, if not all, commercial fryers rely on some sort of oil, often times cooking oil or canola oil, during operation. When the fryer is in operation, the oil experiences gradual degradation over time resulting from use. This degradation results in an overall decrease in the efficiency and effectiveness of the oil for cooking operations. Among those reasons for the lowered effectiveness of the degraded oil include: oxidation and polymerization; cyclic temperature increases; and, hydrolysis.

In order to accurately assess the remaining life of the oil, it becomes necessary to quantify certain properties of the oil in order to determine whether or not the oil is still suitable for use in cooking operations. Several methods for testing the quality of cooking oil exist based upon a number of different properties of the oil. For example, simple means of testing the oil, with relatively unpredictable results, may include evaluating the oil based upon the color, smell, or taste. Slightly more reliable methods of evaluation may include testing the smoke point or viscosity of the oil. While being relatively simple and time effective means of measurement, the results are inherently unreliable and left to the subjective evaluation of the person responsible for administering the test. More reliable means of evaluation therefore rest on certain intrinsic properties of the oil itself.

One particularly useful means of measuring oil quality degradation is to measure the approximate capacitance of the oil, specifically measured by the impurities generated during operation of the fryer. This measurement is referred to as the total polar materials, or TPMs, present in the oil. TPMs are created as a result of the breakup of triglycerides during the frying process into free fatty acids and lipid molecule residues. These substances are able to be measured and classified according to the increased polarity and dielectric constant when compared to that of the original triglycerides in the oil. The result is as follows: when the capacitance measured in the cooking oil increases, the level of TPMs present in the cooking oil has similarly increased.

The use of oil quality sensors for measuring the level of TPMs present in the oil allows for strategic planning and manipulation of the oil throughout a circulation cycle. Additional uses of oil quality sensors may similarly monitor other properties of the oil. For example, a light sensor may be used to monitor the illuminance of the oil or a measure of the polarity of the oil to determine the amount of free fatty acids present.

Accordingly, there is a need in the food service industry for the ability to quickly and effectively remove cooking oil from a fryer following the determination that the oil is no longer suitable for use. A need further exists for the use of oil quality sensors located at positions throughout the oil circulating loop which provide for the most accurate and efficient transport of the oil. Such oil quality sensors may further be operated according to a controller which is capable of determining the relative viability of the used oil and further determining whether or not a particular cycle of oil is capable of being reused, or whether it should be disposed of.

SUMMARY

A system is provided for transporting and measuring the quality of cooking oil between a fryer vat with an exit and an optional return line, a pump having an inlet feed and a discharge, an oil quality sensor, and a storage receptacle having a waste line. The oil quality sensor is capable of measuring the quality of oil passing through the system.

A system is also provided for transporting and measuring the quality of oil between a fryer vat with an exit and an optional return line, an optional feed tank with a feed line, a pump with an inlet feed and a discharge, where the inlet feed draws a suction to drain oil from the exit of the fryer vat to the pump, a storage receptacle with a waste line, at least one oil quality sensor, and a controller. An oil quality sensor may be located in the waste line at the inlet of the storage receptacle. An oil quality sensor may alternatively be located on either the inlet feed or discharge of the pump, or both. The pump discharge, waste line of the storage receptacle, and return line of the fryer vat are all connected via a single flow pathway. The connection of the various pathways may be a three-way control valve which is able to dictate the flow of the various pathways. The controller may dictate such flow of oil between the pathways based at least in part on the quality of oil measured by the oil quality sensor.

A method of transporting oil is also provided. The method involves drawing oil through an exit of a fryer vat to the inlet of a pump. However, the exit of the pump may alternatively be the exit line of a pump housed internal to the fryer. The oil travels through the pump and is released through a discharge line. The discharge line may be connected via a single flow pathway to a waste line of a storage receptacle, a return line to the fryer vat, or travel to a pumping station located external to the fryer unit. An oil quality sensor may be located in the waste line of the storage receptacle and used to measure the relative quality of oil passing through the system. Alternatively, an oil quality sensor may be placed on either of the suction line or discharge of the pump, or both. The quality of oil is then evaluated to determine if it is above or below a predetermined set point corresponding to whether or not the oil is still suitable for cooking operations. The flow of oil is then directed based upon the measured value of oil quality relative to the set point. If the oil quality relative to the set point indicates that the oil is suitable for continued use for cooking operations, the oil is at least partially directed to the return line of the fryer vat. If the oil quality relative to the set point indicates that the oil is no longer suitable for use for cooking operations and should be discarded, the oil is at least partially directed to the waste line of the storage receptacle.

An apparatus is provided having an inlet through which oil may flow into the apparatus, a discharge through which oil may exit the apparatus, a pump capable of drawing oil through the inlet and dispensing oil through the discharge, and an oil quality sensor for measuring the quality of oil. The oil quality sensor may be a TPM sensor.

A system for measuring oil quality is provided. The system includes a fryer unit, a feed tank, a storage receptacle, and a pumping station. The pumping station includes an inlet through which oil may flow into the pumping station, a discharge through which oil may exit the pumping station, a pump capable of drawing oil through the inlet and dispensing oil through the discharge, and an oil quality sensor for measuring the quality of oil. The pumping station is located external to any of the fryer unit, fresh oil feed tank, or storage receptacle.

A method of removing cooking oil from a system is provided. The method first involves initiating the flow of oil through a system. The system includes a fryer unit, a feed tank for providing fresh oil to the system, a storage receptacle for housing oil for disposal, and a pumping station. The pumping station has an inlet through which oil may flow into the pumping station, a discharge through which oil may exit the pumping station, a pump capable of drawing oil through the inlet and dispensing oil through the discharge, and an oil quality sensor for measuring the quality of oil. The method next involves operating the fryer unit for cooking operations, followed by directing the flow of cooking oil from the fryer unit to the pumping station. The next step is measuring the oil quality using the oil quality sensor, evaluating the oil quality measured by the oil quality sensor, and then discharging the cooking oil from the pumping station.

BRIEF DESCRIPTION OF THE DRAWINGS

The invention may take physical form in certain parts and arrangement of parts, embodiments of which will be described in detail in this specification and illustrated in the accompanying drawings which form a part hereof and wherein.

DETAILED DESCRIPTION

Figure 1:
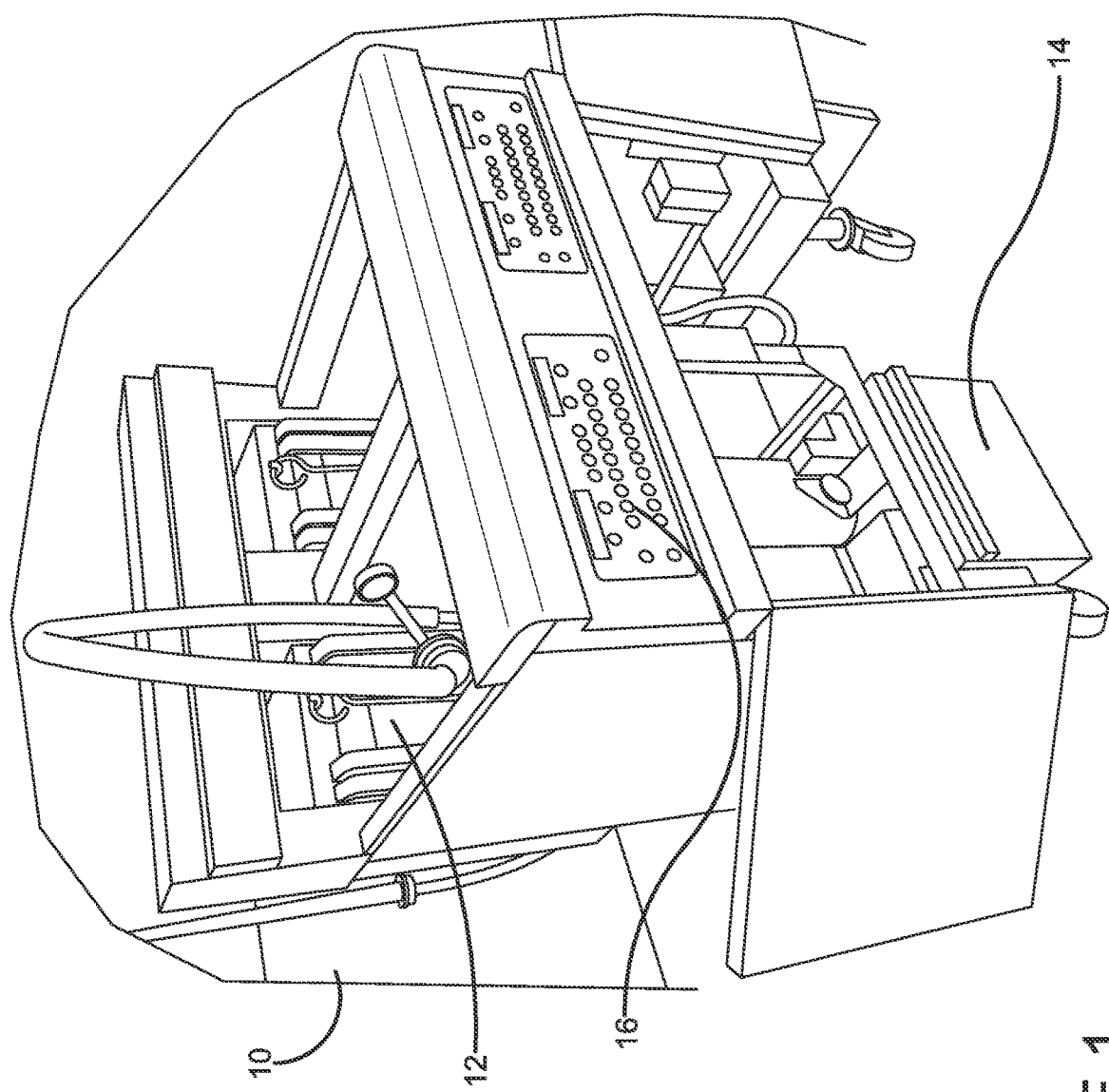
FIG. 1 shows a commercial fryer unit with at least one fryer vat and receiving pan.

Referring now to the drawings wherein the showings are for purposes of illustrating embodiments of the invention only and not for purposes of limiting the same, FIG. 1 shows a commercial fryer unit 10 as is common in the food service industry. Located at the top portion of the fryer 10 is a fryer vat 12. The fryer vat 12 is where cooking operations take place. According to the embodiment shown in FIG. 1, a fryer 10 may have multiple fryer vats 12 located in a single unit. Beneath each of the fryer vats 12 is a receiving pan 14. The fryer vat 12 houses the cooking oil used during operation of the fryer 10. As the oil contained in the fryer vat 12 is subjected to ongoing use, the quality of the oil begins to decrease. Once the oil quality has decreased to a predetermined level corresponding to the useful life of the oil, as identified by any different number of properties used for measuring oil quality, the oil contained within the fryer vat may be referred to as "waste oil." The fryer 10 may include a fryer unit control interface 16 which allows for user control of the cooking operations of the fryer.

Figure 2:
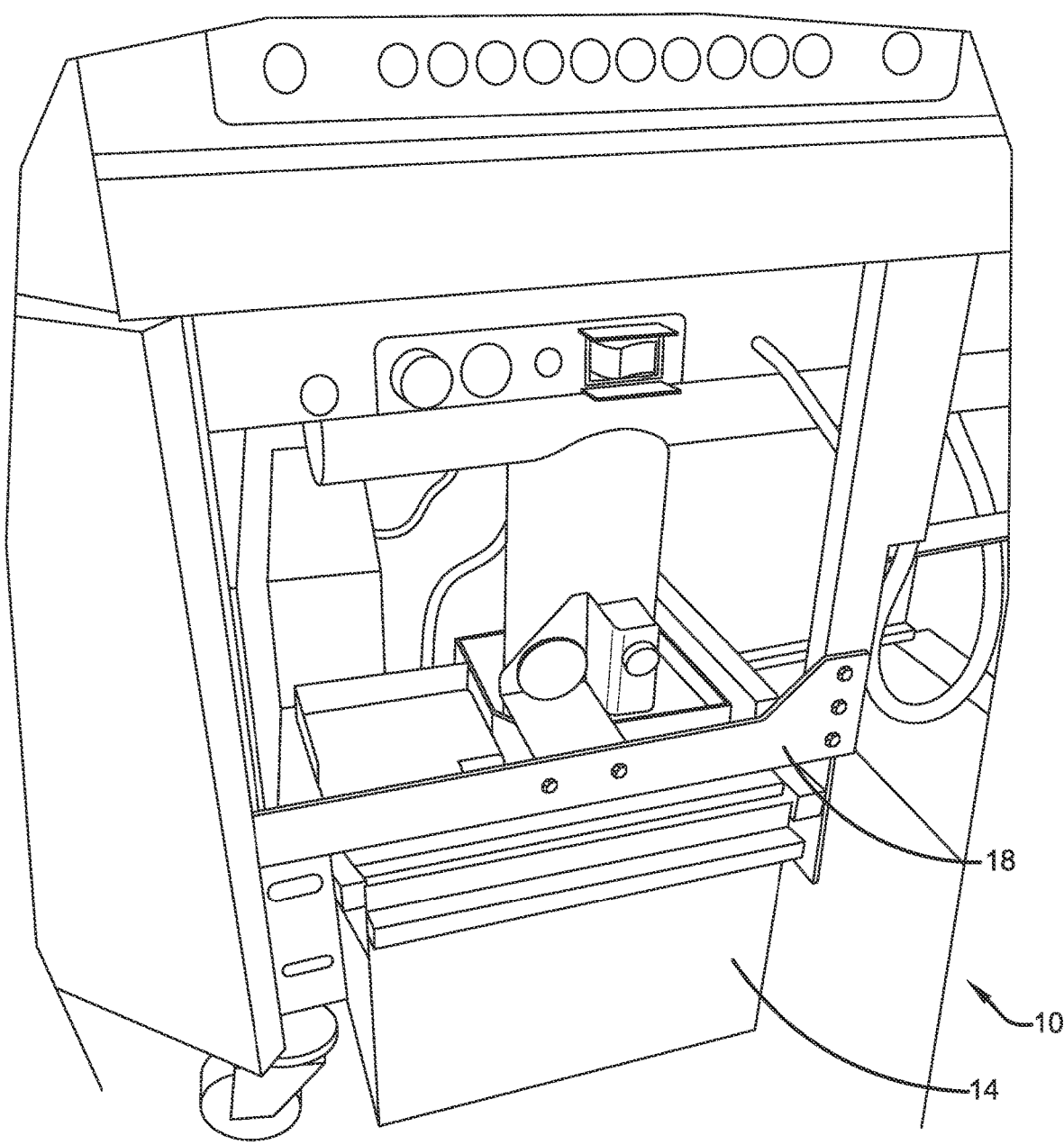
FIG. 2 is an alternative view of a fryer unit showing the receiving pan located beneath the fryer vat.
Figure 3:
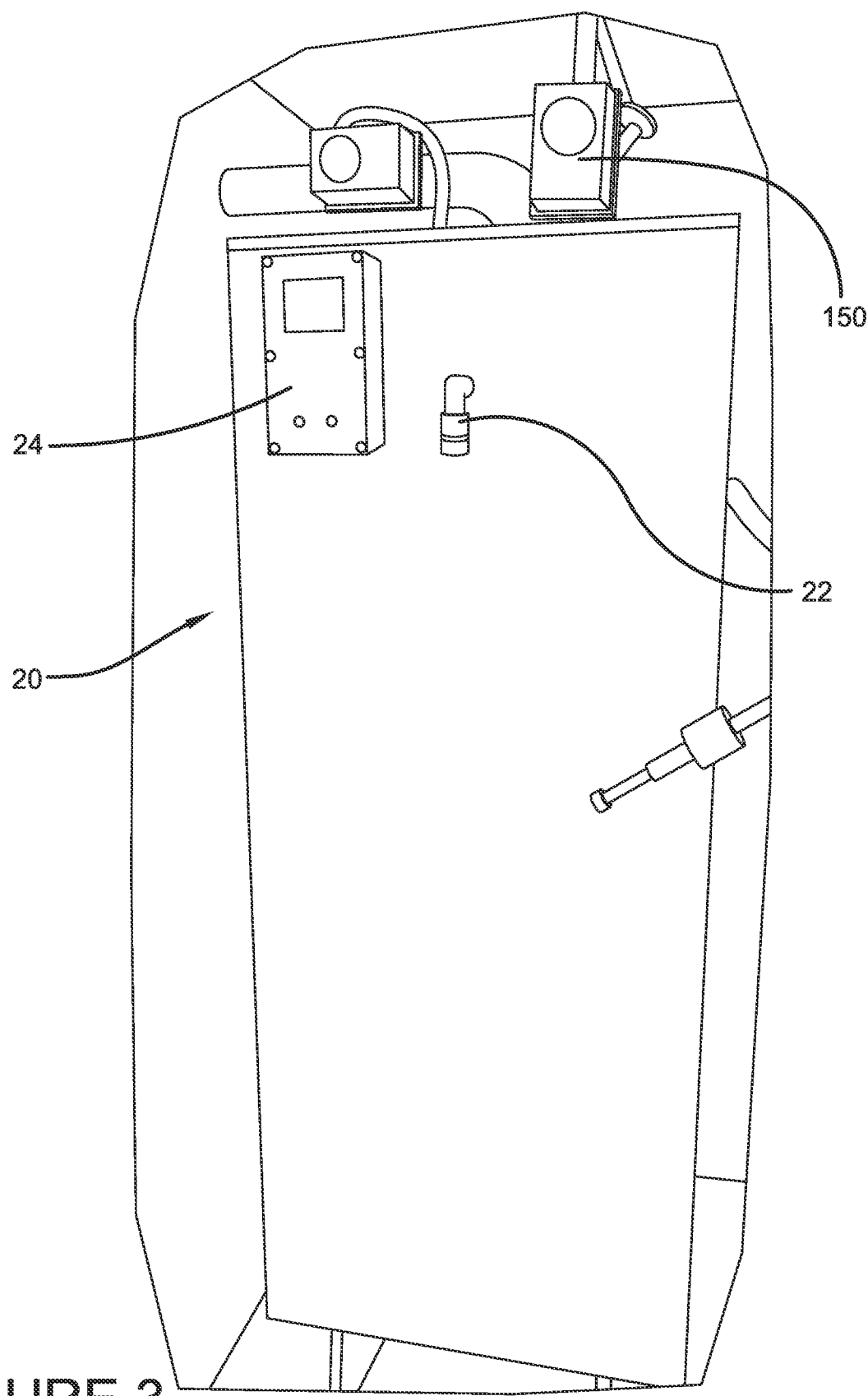
FIG. 3 shows a storage receptacle capable of housing cooking oil.

With reference now to FIG. 2, the pan 14 can be seen positioned about the bottom of the fryer 10. The receiving pan 14 is typically placed inside a housing 18 which provides a secure placement for the receiving pan 14 during operation. When the oil quality has reached a level which requires an exchange of oil, the cooking oil is removed from the fryer vat 12 and placed in a storage receptacle 20, as shown in FIG. 3. The storage receptacle 20 may contain at least one inlet, first inlet 22 through which the cooking oil may be transferred into the storage receptacle 20. Storage receptacle 20 may have a second inlet 150 through which cooking oil may flow directly from the fryer vat and into the storage receptacle 20. The storage receptacle 20 may have either first inlet 22, second inlet 150, or both first inlet 22 and second inlet 150. A storage receptacle controller 24 may be incorporated into the storage receptacle 20. The storage receptacle controller 24 may be capable of monitoring the level of the cooking oil currently stored, the oil quality of the oil located within the receptacle (such as the TPMs, color of the oil, concentration of free fatty acids ("FFAs"), etc.), or any other properties or characteristics of the oil as desired. The fryer unit control interface 16 may be integrated with that of the storage receptacle controller 24 to further integrate the system.

One useful method for measuring the quality of oil is by way of measuring the electrical properties of the oil, and in particular the dielectric constant. Various types of sensors may be employed to measure such electrical properties, such as a capacitance sensor, open-ended coaxial sensor, conductivity sensor, or a resonant-type sensor. By placing a sensor in any of the various transfer lines throughout the system, the accumulation of polar materials which result from the breakup of fatty acids and lipid molecules in the oil during heating operations may be monitored. This accumulation results in the elevation of the polarity of the oil, which manifests itself as an increase in the dielectric constant of the oil. The sensor thus measures the change in TPMs as the oil travels through the transfer line. The control unit may be programmed with a preset value of TPMs which indicates the proper time to begin an oil changeover based upon whether the oil is suitable for further cooking operations.

Figure 4:
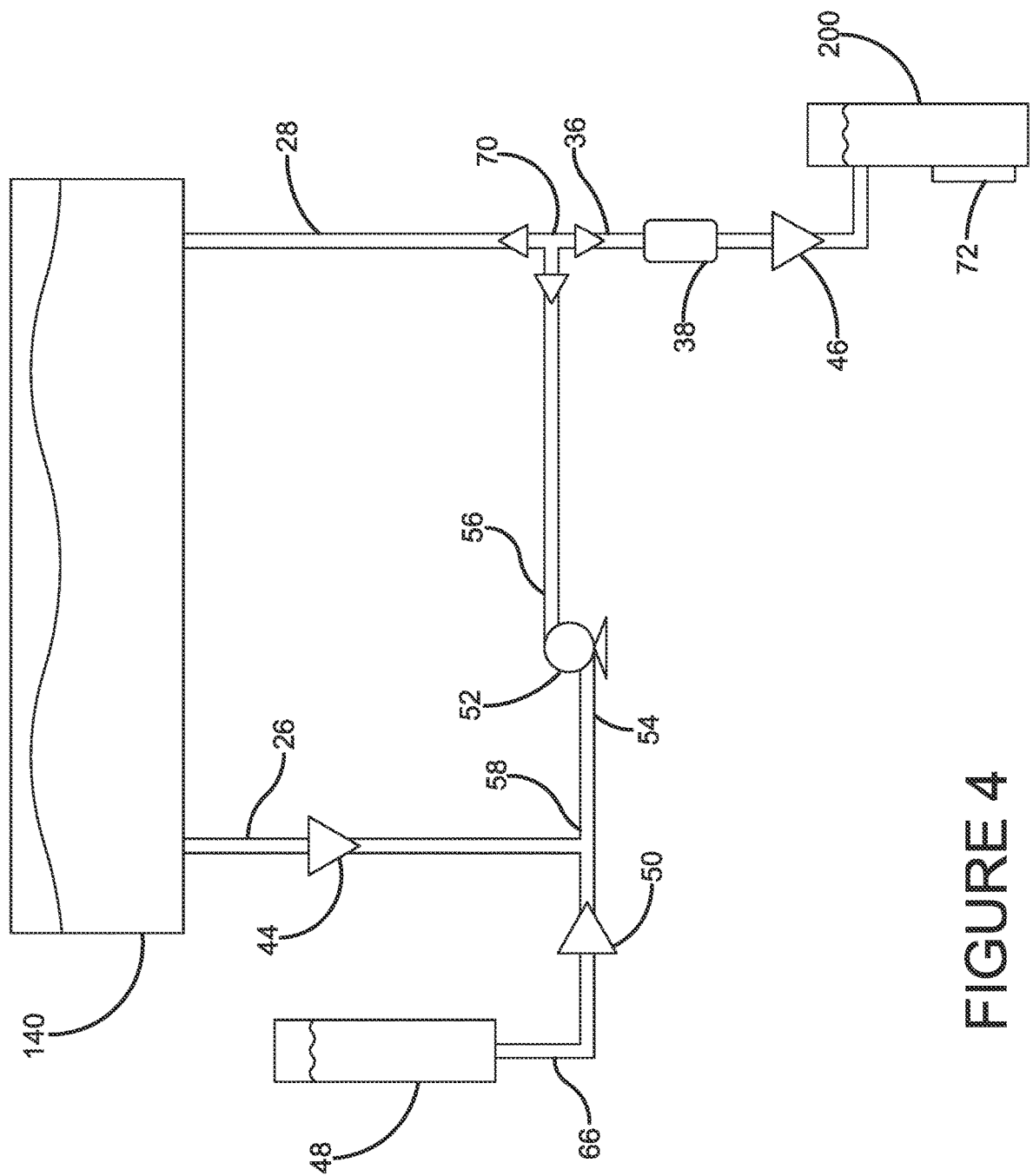
FIG. 4 shows a system of measuring the quality of oil inside a recycle loop.

With reference now to FIG. 4, a system for monitoring the oil quality of cooking oil leaving a fryer vat is shown. The cooking oil exits the fryer vat 140 through drain line 26. The flow of cooking oil through drain line 26 may be controlled by a drain line control valve 44. When drain line control valve 44 is set to an open configuration, the cooking oil will proceed to flow into pump 52 via the pump inlet feed 54. Pump 52 is independent of the fryer vat 140. According to one embodiment, a fresh oil feed tank 48 may be positioned up stream of the pump inlet feed 54. The flow of fresh oil from the fresh oil feed tank 48 travels through fresh oil feed tank exit feed 66 and may be controlled by fresh oil feed line control valve 50. Feed line control valve 50 may be set to a closed configuration such that only cooking oil flowing through drain line 26 is sent to the pump 52. A controller 72 may be integrated into the system in order to constantly monitor and control the various operations of the components, for example by placement on the storage receptacle 200.

With continued reference to FIG. 4, oil may be drawn from the fryer vat 140 through drain line 26 by way of a suction line from pump 52. According to one embodiment, the drain line 26 is a suction wand configured to the inlet of the pump 52. The suction wand draws cooking oil from the fryer vat 140 into the pump 52. As this suction line draws the oil from the fryer vat 140 through drain line 26, this suction line becomes the pump inlet feed 54. According to the embodiment where the drain line 26 is a suction wand, the inlet feed 54 to the pump 52 and drain line 26 are collectively replaced by the suction wand. The cooking oil then leaves the pump 52 through pump discharge 56. The cooking oil will then flow through a three-way control valve 70. The three-way control valve 70 may split the flow of cooking oil into two pathways: a waste line 36 and a return line 28. According to one embodiment, the three-way control valve 70 will direct the flow of cooking oil to the waste line 36. An oil quality sensor 38 will be located in the waste line 36 to measure the quality of oil passing through the waste line 36. The oil quality sensor 38 may monitor any different number of properties or characteristics of the oil, such as TPMs, color, FFAs, or any other properties as identified by those having skill in the art.

A control valve may be placed either upstream or downstream of the oil quality sensor 38 in the waste line 36. According to the embodiment shown in FIG. 4, waste line control valve 46 is placed immediately after oil quality sensor 38 and may be used to either restrict or direct the flow of cooking oil through the waste line 36 to the storage receptacle 200. Based upon the quality of oil measured by the oil quality sensor 38, the configuration of the waste line control valve 46 (i.e., either open or closed) may be determined. If the oil quality is found to be within a usable level based upon the specific property or characteristic being measured according to those having skill in the art, then the waste line control valve 46 may be set to a closed configuration in order to restrict the flow of oil to the storage receptacle 200. Alternatively, if the oil quality is found to be outside a usable level based upon the specific property or characteristic being measured according to those having skill in the art, then the waste line control valve 46 may be set to an open configuration in order to direct the flow of cooking oil through waste line 36 and into the storage receptacle 200.

According to one embodiment, the property of the oil being measured is that of the TPMs present in the oil. The oil quality sensor 38 measures the TPMs present in the oil as it flows through the waste line 36. The controller 72 may be integrated into the system and programmed with a predetermined set value indicating whether or not the oil is still usable for cooking operations. When the oil quality sensor 38 measures the TPMs to be above this set point, the controller 72 may send a signal to waste line control valve 46, opening the waste line control valve 46 and directing the flow of cooking oil through waste line 36 and into the storage receptacle 200. Alternatively, if the oil quality sensor 38 measures the TPMs to be below the set point, the controller 72 may send a signal to waste line control valve 46, closing the waste line control valve 46 and restricting the flow of oil through waste line 36 and into the storage receptacle 200, as this oil is deemed to still be viable for cooking operations.

With continued reference to FIG. 4, the controller 72 may further control the configuration (open/closed) of the drain line control valve 44 and fresh oil feed line control valve 50. Based upon the oil quality measured by oil quality sensor 38, the controller 72 may send a signal to the fresh oil feed valve 50 to open, allowing the flow of fresh feed oil from the feed storage tank 48 through fresh oil tank exit feed 66. This flow of fresh feed oil may combine with the oil flowing through drain line 26 to form blended oil stream 58. An alternative embodiment may replace control valves 44 and 50 with a single three-way control valve, similar to that of the three-way control valve 70 used for dictating the flow of oil between the return line 28 and waste line 36. The controller 72 may operate the system as a continuous feedback loop, constantly adjusting the control of the various control valves according to the measurements recorded by oil quality sensor 38 to ensure that an optimum amount of oil is able to be recycled back into the fryer vat 140 through return line 28.

Figure 5:
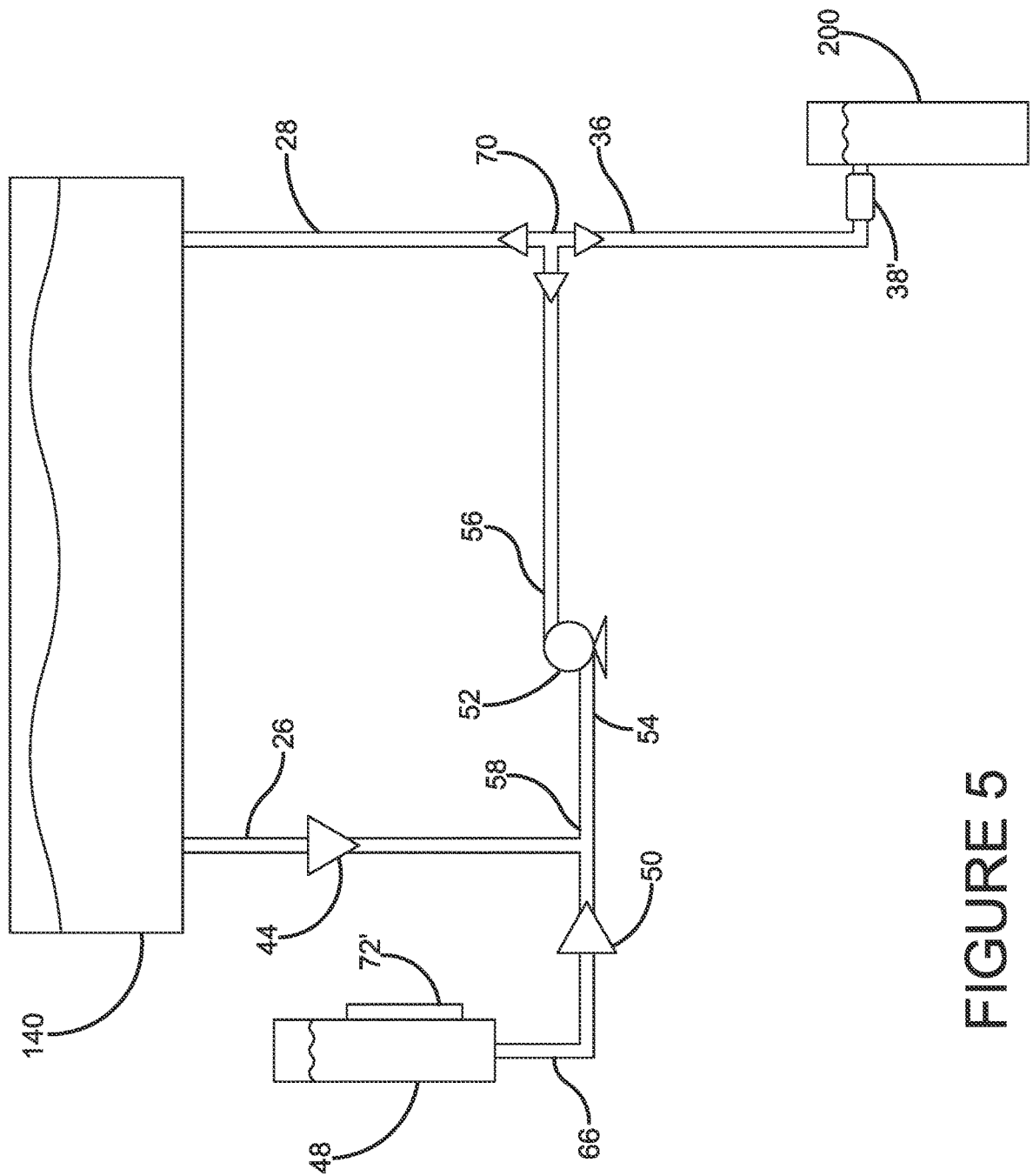
FIG. 5 shows an alternative system of measuring the quality of oil inside a recycle loop.

With reference now to FIG. 5, an alternative embodiment of the system for measuring the quality of oil is shown. The system may still utilize the transport path of oil from the three-way control valve 70 to the storage receptacle 200 through waste line 36, as shown in FIG. 4. Oil quality sensor 38' is located about the inlet to the storage receptacle 200. The oil quality is measured by oil quality sensor 38' directly before the cooking oil enters the storage receptacle 200. Controller 72', similar to that of controller 72 discussed above but alternatively placed on the fresh oil feed tank 48, may dictate the flow of oil through the system similar to that discussed above with regards to the embodiment shown in FIG. 4: based upon the measured value of oil quality by oil quality sensor 38', the configuration of the three-way control valve 70 (open/closed) may be adjusted. For example, if oil quality sensor 38' is measuring the TPMs of the cooking oil, three-way control valve 70 may restrict the flow of oil to return line 28 when the TPMs are measured to be above a set point indicating a usable level for cooking operations. Alternatively, three-way control valve 70 may permit the flow of oil to return line 28 when the TPMs are measured to be below a set point indicating a usable level for cooking operations.

Figure 6:
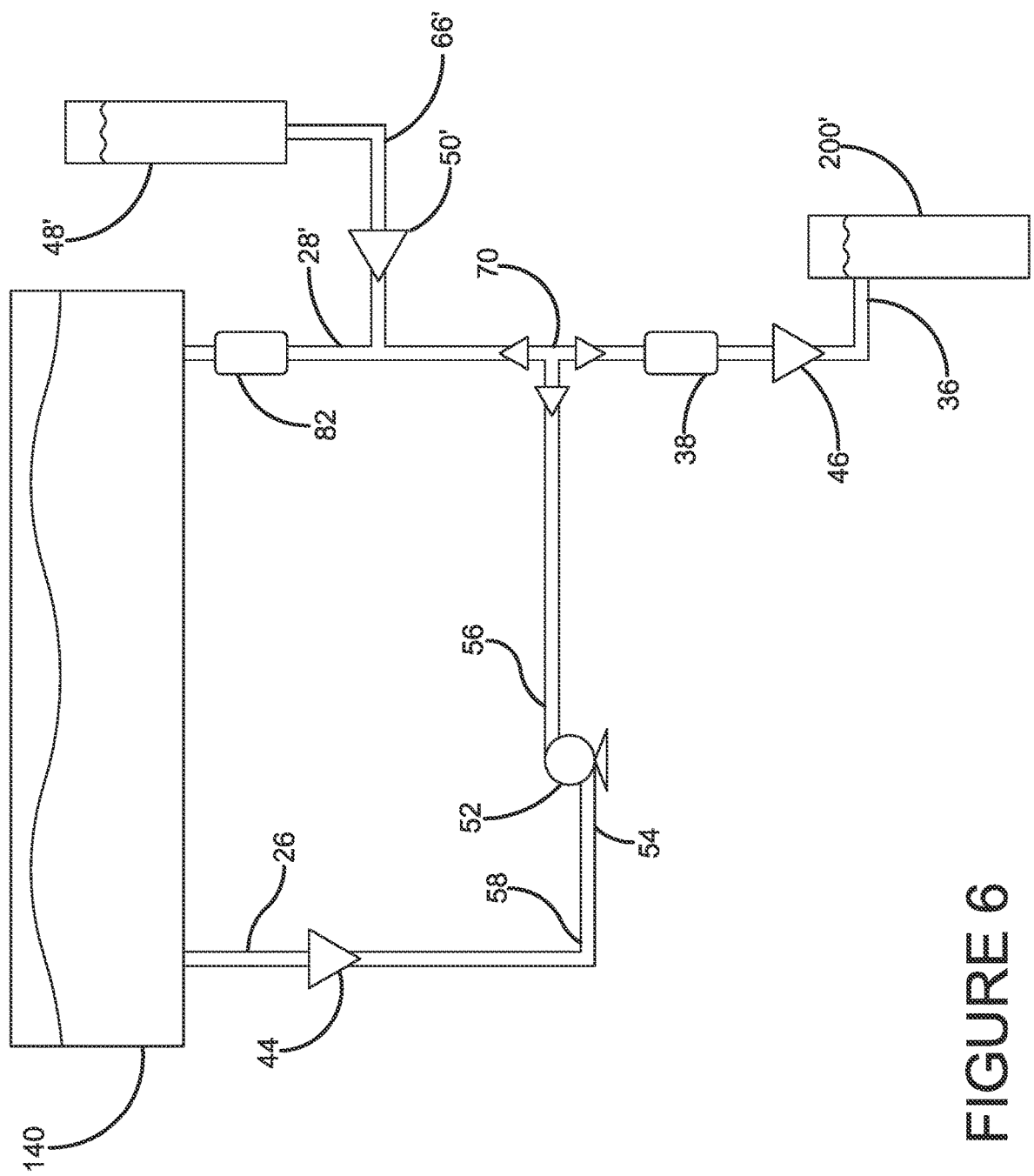
FIG. 6 shows another alternative system of measuring the quality of oil inside a recycle loop.

With reference now to FIG. 6, an alternative configuration of the oil transport system is shown. Oil leaves the fryer vat 140 through drain line 26, passing through control valve 44 when the valve is in an open configuration, and enters pump 52 via pump inlet feed 54. According to one embodiment, the drain line 26 is a suction wand configured to the inlet of the pump 52. The suction wand draws cooking oil from the fryer vat 140 into the pump 52. According to the embodiment where the drain line 26 is a suction wand, the inlet feed 54 to the pump 52 and drain line 26 are collectively replaced by the suction wand. The oil then exits the pump 52 via discharge line 56, where the oil meets a juncture comprising three-way valve 70. Three-way valve 70 may direct the flow of oil into one of two paths: recycle line 80, or waste line 36. The configuration of the three-way control valve 70 is determined by the quality of oil measured by oil quality sensor 380 which is fitted to the waste line 36. Waste line 36 may optionally contain an additional control valve, waste line control valve 46, which is capable of directing the flow of cooking oil to the storage receptacle 200', or restricting the flow from storage receptacle 200'. Waste line control valve 46 may be placed either before or after oil quality sensor 380 relative to the position of the storage receptacle 200'.

According to one embodiment, oil quality sensor 380 measures the capacitance of the oil flowing through waste line 36 as the TPMs present in the oil. A predetermined set point is chosen which indicates whether or not the oil remains suitable for continued cooking operations. The set point may be chosen based upon a number of different factors, including but not limited to: type of oil, intrinsic properties of the oil, temperature of the oil, pressure of the oil, or any other properties as identified by those having skill in the art for having an effect on the suitability of the oil for cooking operations. If the quality of oil passing through oil quality sensor 380 indicates a level of TPMs above the set point, then the oil is rendered no longer suitable for continued cooking operations and directed towards storage receptacle 200' by opening waste line control valve 46. If the quality of oil passing through oil quality sensor 380 indicates a level of TPMs below the set point, then the oil is considered to still be suitable for cooking operations. When the oil is considered to still be suitable for cooking operations, waste line control valve 46 is set to a closed configuration and the three-way control valve 70 is configured so as to permit the flow of oil to recycle line 80. Additional embodiments may combine the two approaches outlined above, where oil is permitted to travel both through waste line control valve 46 and enter recycle line 80.

With continued reference to FIG. 6, fresh oil feed tank 48' may be located downstream of the recycle line 80. When additional oil is needed to enter the fryer vat 140, fresh oil feed tank 48' may introduce such fresh oil via fresh oil feed tank exit feed 66'. Fresh oil feed line control valve 50' is responsible for controlling the flow of fresh feed oil to the system. When an introduction of fresh oil is desired, fresh oil feed line control valve 50' is set to an open configuration, and the fresh oil of fresh oil feed tank exit feed 66' is combined with that of the recycle line 80 to form return line 28'. Optionally, a second oil quality sensor, return line oil quality sensor 82, may be placed in the return line 28' to monitor the quality of oil entering the fryer vat 140.

According to the various embodiments discussed throughout the present disclosure, any of the controllers referenced herein are capable of interfacing with the various components used in the system in order to control the flow of cooking oil throughout the system. The various controllers discussed with reference to the particular embodiments shown in the FIGURES are but examples of the various different locations in which the controller may be placed. Various different configurations of the controllers may be used, in addition to the combination of multiple controllers used in conjunction with one another. The various controllers may generate and send signals to the various control valves throughout the system according to the measurements of the various oil quality sensors. This configuration allows for the system to be run as a continuous feedback loop, with the controller constantly providing feedback to the control valves based upon the changing measurements of the oil quality sensors.

Figure 7:
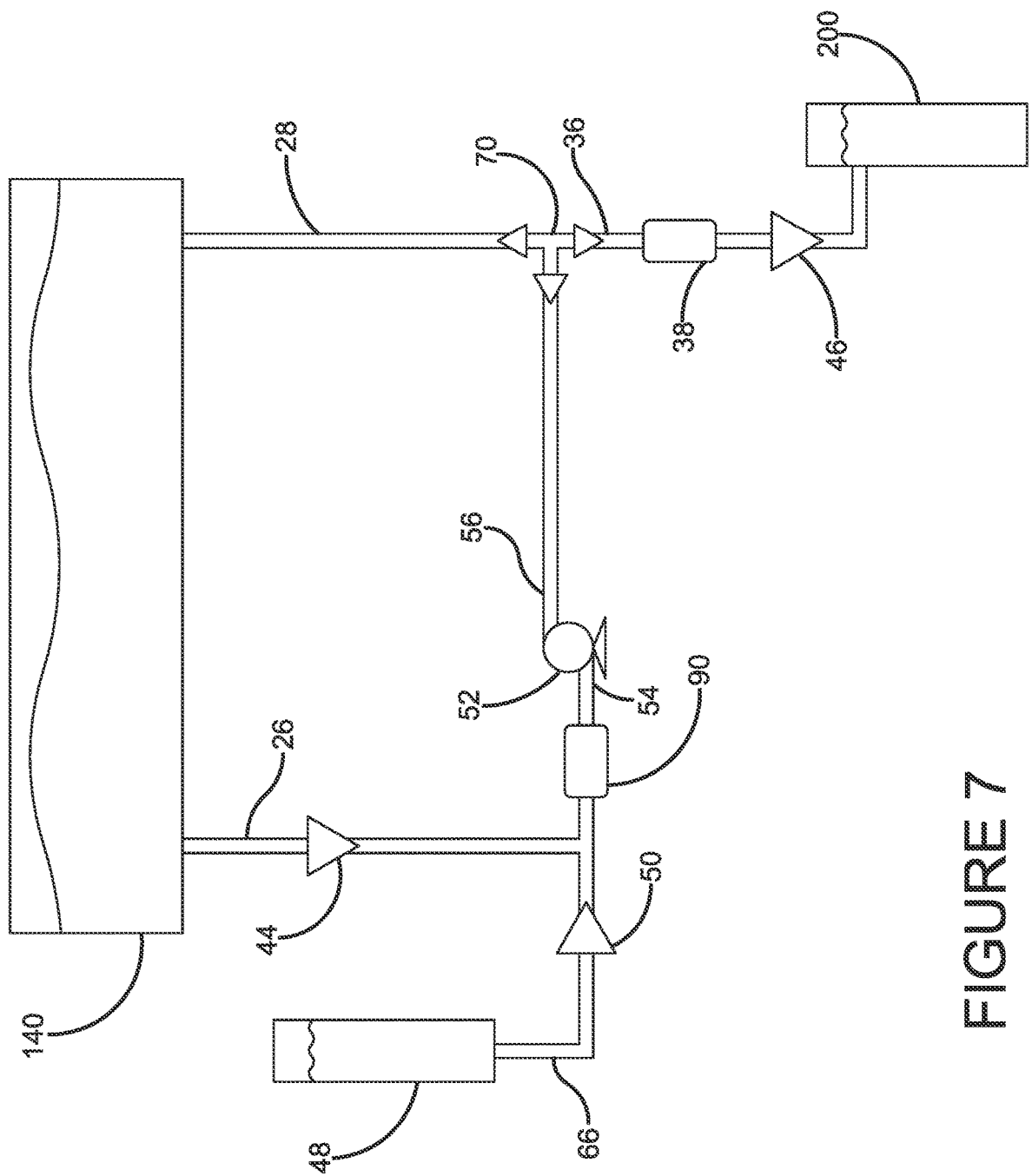
FIG. 7 shows another alternative system of measuring the quality of oil inside a recycle loop.

With reference now to FIG. 7, an additional oil quality sensor may be introduced upstream of the pump 52; pre-pump oil quality sensor 90. While the embodiment shown in FIG. 7 shows the pre-pump oil quality sensor 90 according to a system configuration wherein the fresh oil feed tank 48 is shown upstream of the pump 52, those having ordinary skill in the art will recognize that such a pre-pump oil quality sensor 90 may be equally applicable to a system configuration which places the fresh oil feed tank downstream of the pump 52, as shown in the configuration of FIG. 6. The pre-pump oil quality sensor 90 is used to measure the oil quality prior to entering the pump 52 through pump inlet feed 54.

According to one embodiment, the pre-pump oil quality sensor 90 is a traditional "in-line" oil quality sensor, such as that of waste line oil quality sensor 38. According to another embodiment, the pre-pump oil quality sensor 90 may be a wand sensor located in the suction line of the pump 52, wherein the drain line 26 and pump inlet 54 are replaced by the suction wand described above, with the suction wand further being equipped with a wand sensor for measuring the quality of oil being drawn through the suction want and into the pump. The pre-pump oil quality sensor 90 may be used either as the lone oil quality sensor in the system, or incorporated with any different number of combinations of additional oil quality sensors discussed throughout this disclosure, such as an additional oil quality sensor located about the discharge of the pump 56. A controller may be integrated into the system so as to control the operation of the various components, including any of the oil quality sensors and operation of the various control valves which dictate the flow of oil throughout the system.

Figure 8:
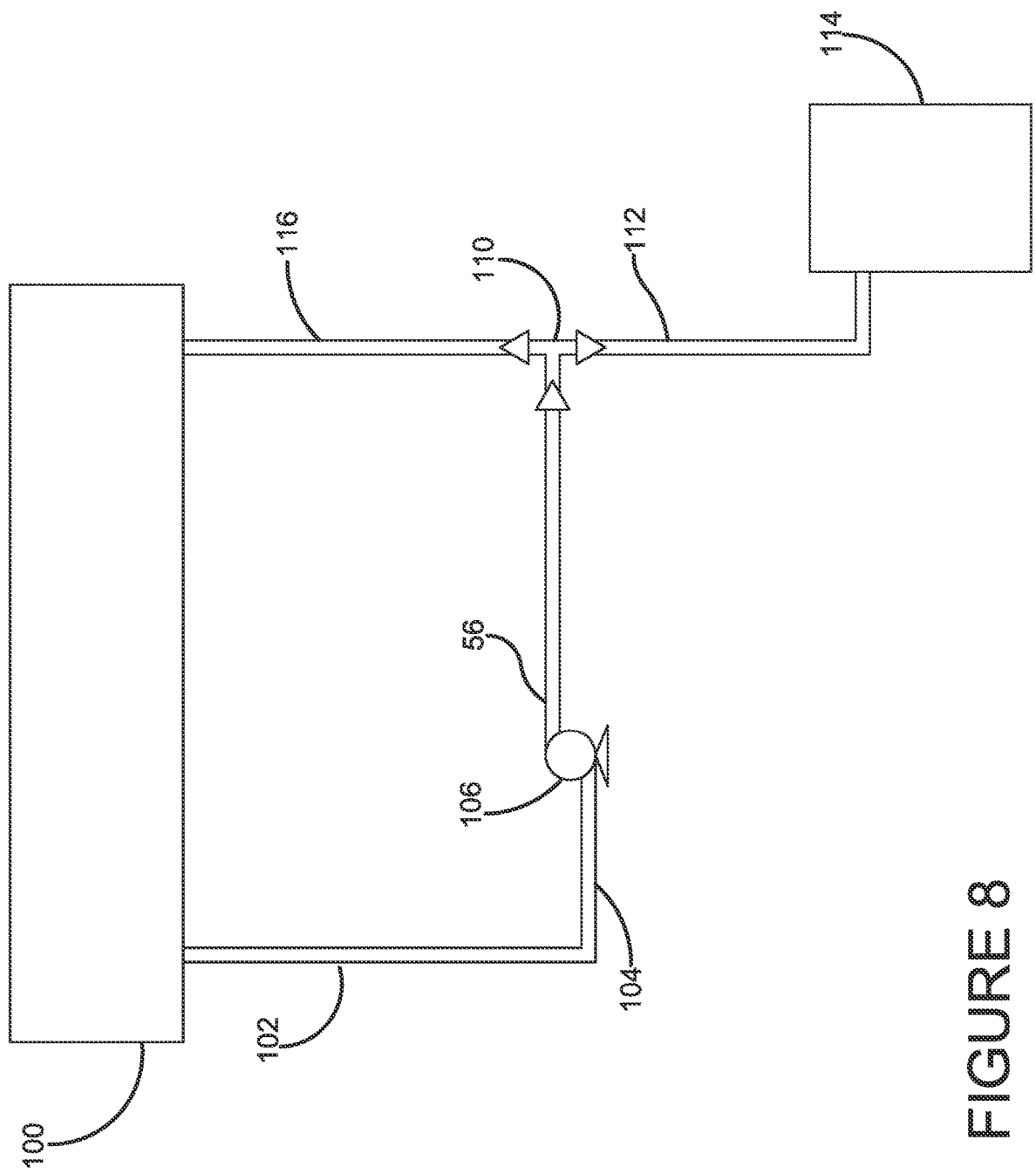
FIG. 8 illustrates an alternative system of measuring oil quality.

With reference now to FIG. 8, a cooking oil pumping station is shown having a fryer unit 100, pump 106, and storage receptacle 114. The fryer unit 100 is capable of performing cooking operations and has used cooking oil, or waste oil, exit through fryer unit discharge 102. Upon exiting the fryer unit 100, fryer unit discharge 102 transitions into pump inlet feed 104, which routes the cooking oil to pump 106. Pump 106 is located external to either of the fryer unit 100 or storage receptacle 114.

Figure 9:
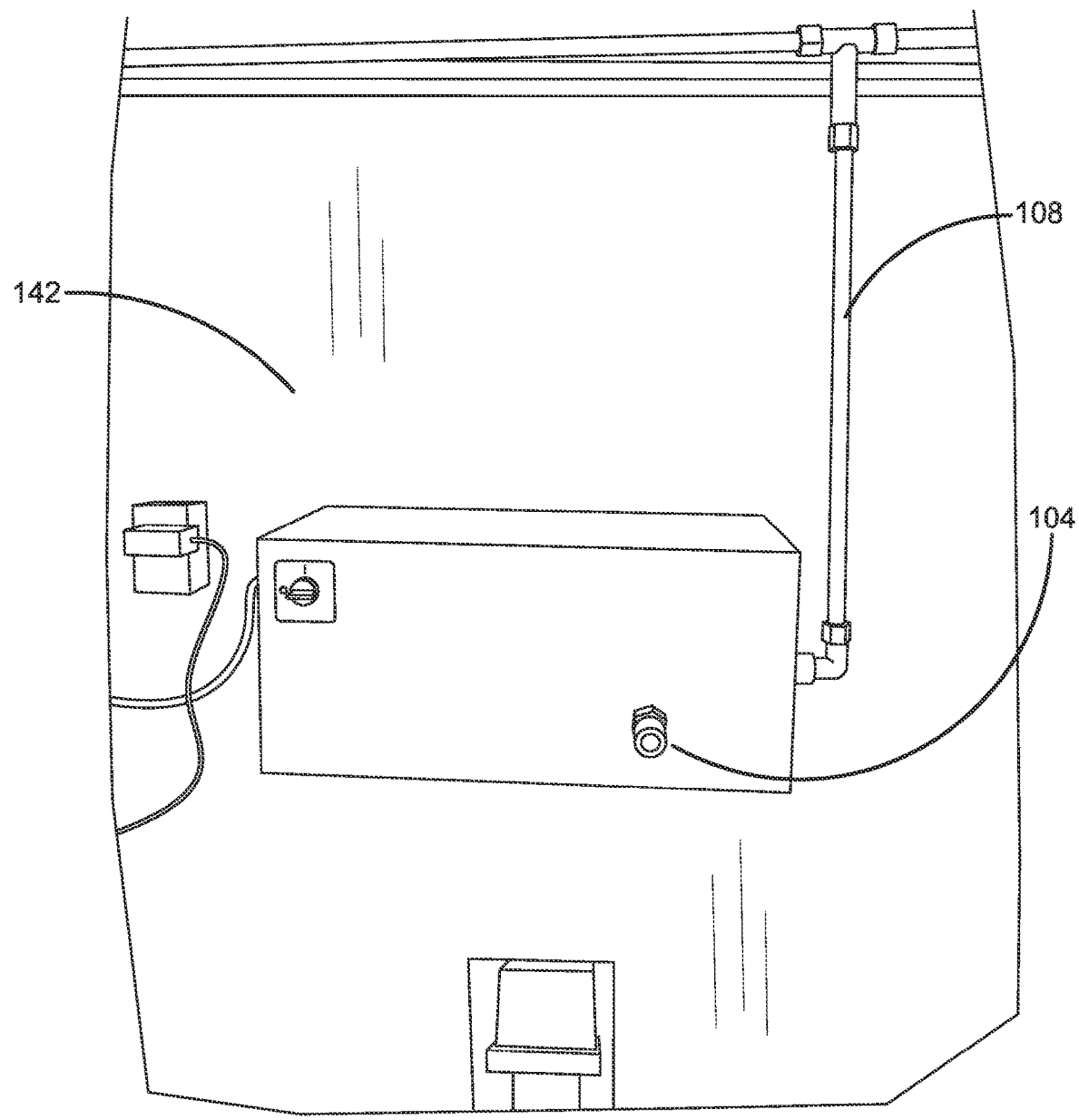
FIG. 9 illustrates a pumping station for directing the flow of oil through a system for measuring oil quality.

Pump 106 may alternatively be a pumping station 142, such as that shown in FIG. 9. Pumping station 142 provides a central housing which may contain a pump 106. Pumping station 142 may further include an oil quality sensor. The oil quality sensor is able to measure the quality of oil located inside pumping station 142. For example, the oil quality sensor may be a TPM sensor. According to one embodiment, the oil quality sensor is an in-vat oil quality sensor which measures the quality of oil housing within pumping station 142. According to an alternative embodiment, the oil quality sensor is an inline oil quality sensor. The inline oil quality sensor may be placed in either the inlet feed 104 to the pumping station 142, or alternatively in the discharge 108 from the pumping station 142.

With continued reference to FIGS. 8 and 9, the pump discharge 108 enters a three-way control valve 110. The two flow paths following control valve 110 are that of a recycle line 116, which flows back into the fryer unit 100, or alternatively waste line 112, which flows into storage receptacle 114. According to the quality of oil as measured by the oil quality sensor, the correct flow path for the oil is dictated by the configuration of control valve 110: if the oil quality is determined to still be suitable for use in cooking operations, the control valve 110 is configured to direct the flow of oil back to the fryer unit 100; however, if the oil quality is determined to no longer be suitable for use in cooking operations, the control valve 110 is configured to direct the flow of oil to storage receptacle 114 for disposal. An alternatively embodiment may allow for the flow to be split to both the recycle line 116 and the waste line 112. The system may further incorporate a controller which is responsible for determining the proper path of flow of oil based upon the measured oil quality by the oil quality sensor.

Figure 10:
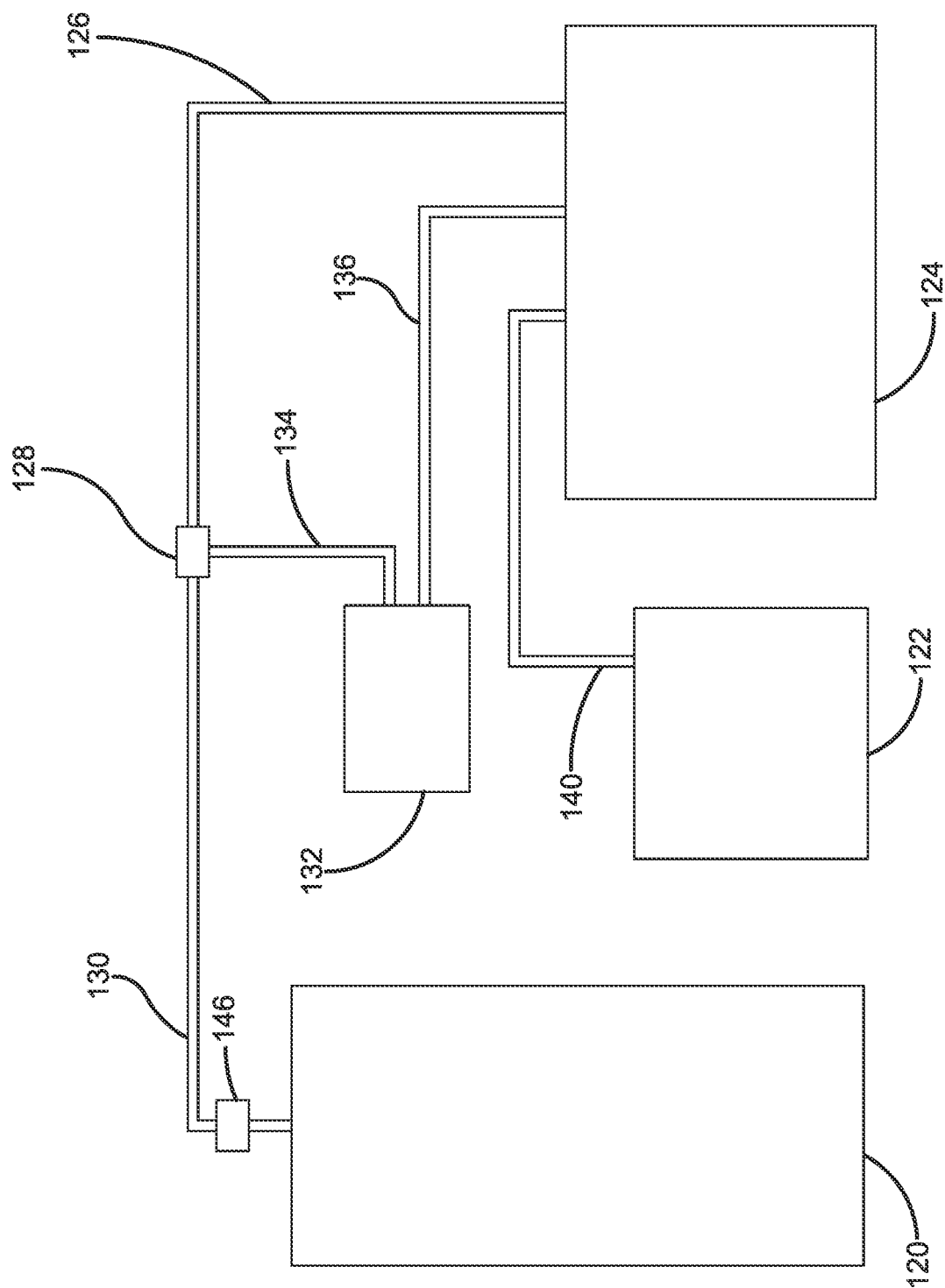
FIG. 10 is an alternative system of measuring oil quality, showing both a pumping station located external to the fryer unit and a direct flow pathway from the fryer unit to the storage receptacle.
Figure 11:
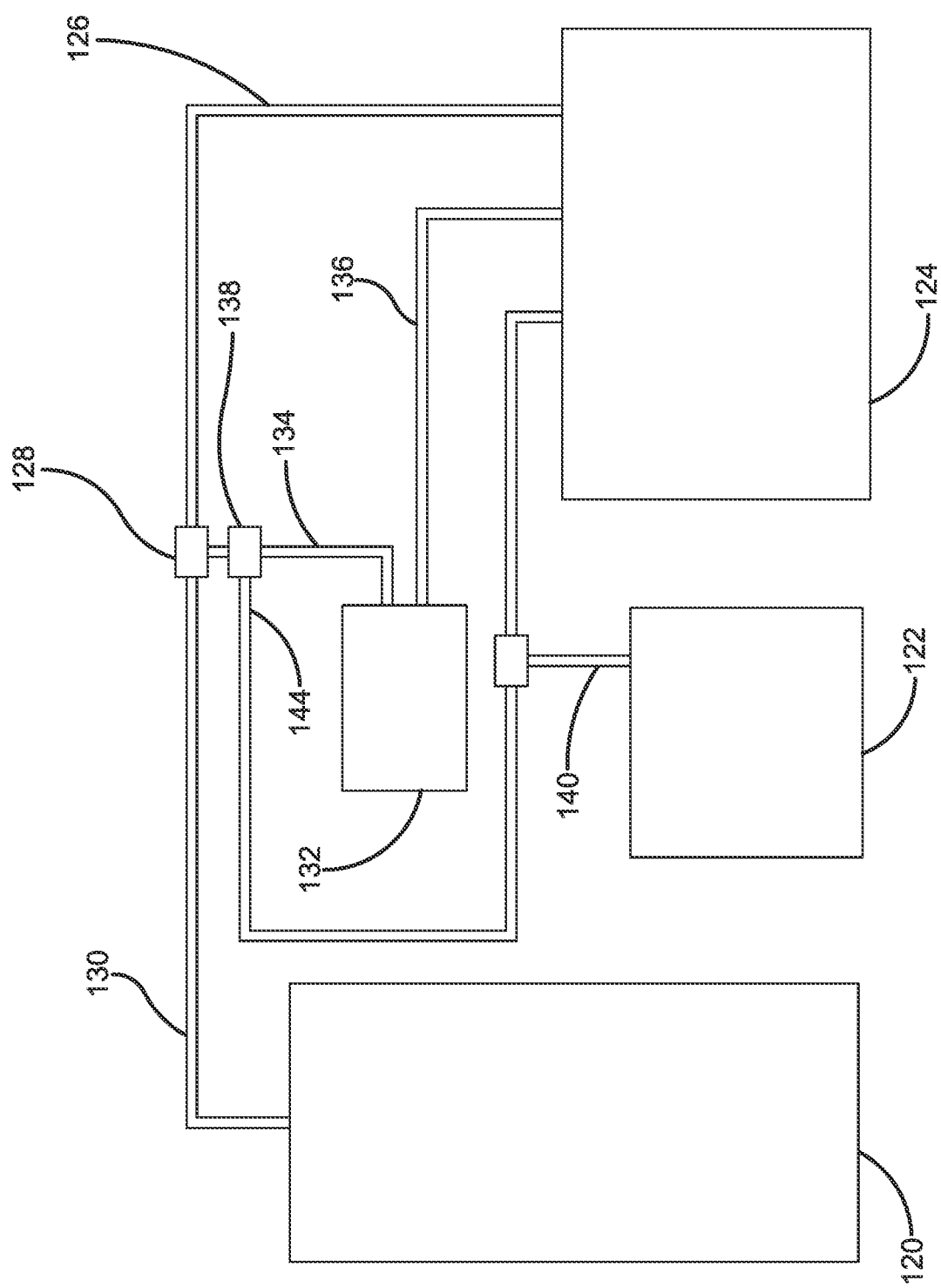
FIG. 11 is another alternative system of measuring oil quality.

With reference now to FIGS. 10 and 11, an alternative embodiment of a cooking oil pumping station is shown. The cooking oil pumping station comprises a storage receptacle 120 for housing cooking oil, a fresh oil feed 122 for dispensing fresh feed oil to the system, and a fryer unit 124 used for cooking operations. Fresh oil is dispensed from the fresh oil feed tank 122 through fresh oil feed line 140 and into the fryer unit 124 for use in cooking operations. After use, the cooking oil may be dispensed according to either of two paths: either of fryer unit direct plumb line 126, or pumping station inlet feed 136, or both. Oil flows through pumping station inlet feed 136 and into pumping station 132. Pumping station 132 may incorporate any of the various components as that of pumping station 142 as shown in FIG. 9.

Upon entry into pumping station 132, the quality of the cooking oil may be measured by an oil quality sensor. The cooking oil then exits the pumping station 132 via pump discharge 134. According to the embodiment shown in FIG. 10, the cooking oil then presents itself to a first control valve 128, which interfaces the flow between fryer unit direct plumb line 126 and pump discharge 134. These two flow pathways combine at the juncture of control valve 128 and the combined flow comprises final waste line 130, which flows into the storage receptacle for disposal. By measuring the oil quality passing through pumping station 132, the amount of fresh oil to be introduced into the system via fresh oil feed line 140 can be better evaluated. For example, a controller may be integrated with the system which is able to dictate the flow of the various pathways according to the measured quality of the oil.

According to the embodiment shown in FIG. 11, oil flowing through pump discharge 134 may come to a juncture at recycle control valve 138. Based upon the quality of oil flowing through pump discharge 134, recycle control valve may direct the flow into one of two pathways: through the recycle control valve 138 and on to the interface with first control valve 128 to combine with fryer unit direct plumb line 126 to create final waste line 130, or to branch off into recycle line 144. When oil is permitted to flow into recycle line 144, this flow pathway may combine with fresh oil feed 140, such as at a control valve, or alternatively flow directly back into the fryer unit 124 for continued use. The system may be integrated with a controller capable of directing the flow between the various pathways according to the measured quality of the oil.

Returning now to FIG. 10, the system may have a waste line oil quality sensor 146 located directly before the inlet to the storage receptacle 120, measuring the oil quality of oil flowing through final waste line 130. Waste line oil quality sensor may be placed either prior to, or after, a control valve which controls the flow of oil through waste line 130 and into storage receptacle 120.

Figure 12:
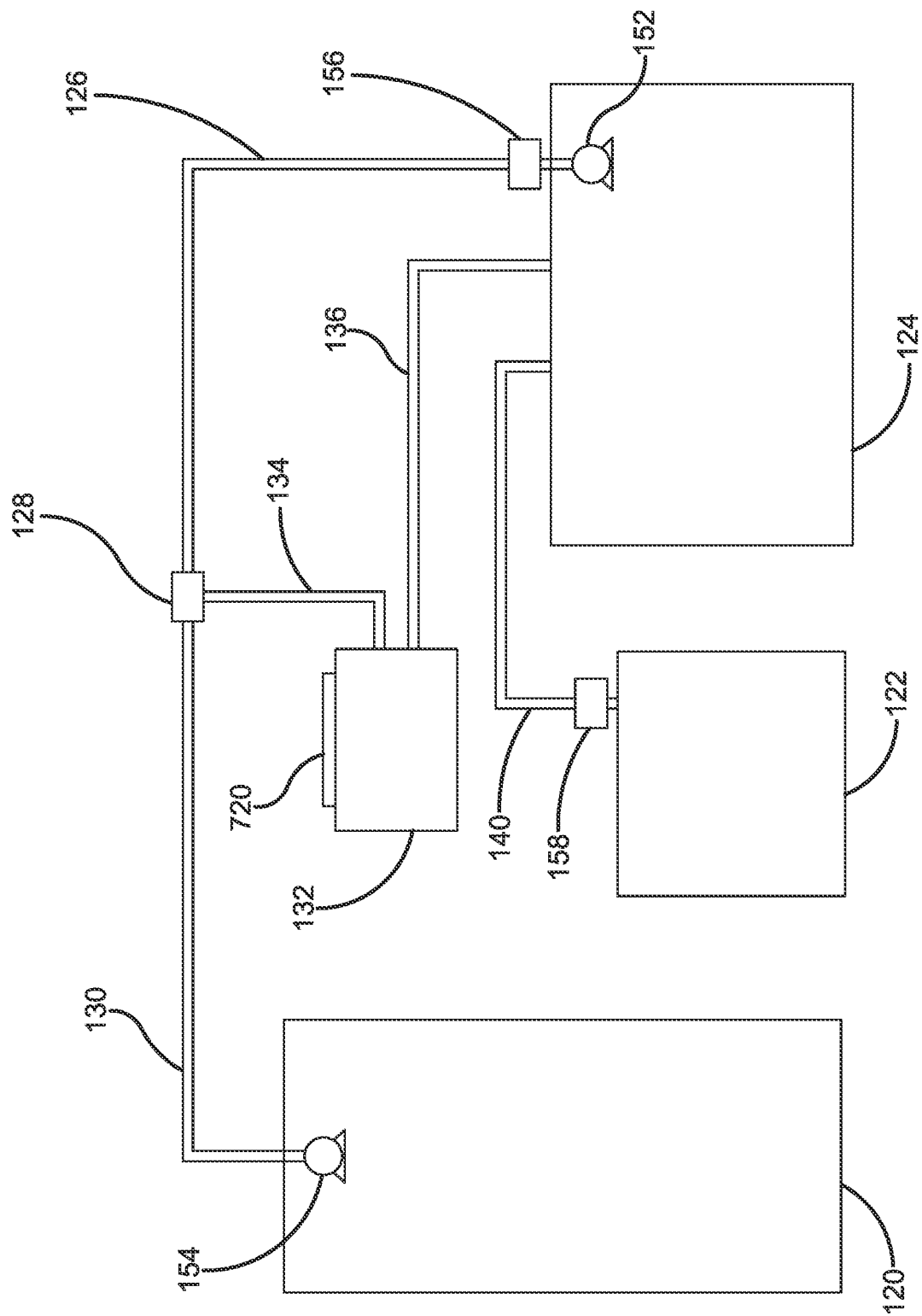
FIG. 12 is another alternative system of measuring oil quality.

With reference now to FIG. 12, an alternative embodiment of a system for measuring oil quality is shown. The fryer unit direct plumb line 126, which transfers cooking oil directly from the fryer unit 124 to the storage receptacle 120, may operate according to a system in the absence of a waste oil pumping station 132. According to such an embodiment, the only flow pathway for cooking oil out of the fryer unit (excluding any fresh oil feed into the fryer unit) may be the direct line 126 to the storage receptacle 120. However, an alternative embodiment may utilize only an external pumping station 132, thus not having a direct line 126. Yet another alternative embodiment may have both the direct line 126 and the pumping station 132, as shown in FIG. 12.

With continued reference to FIG. 12, the fryer unit 124 may house a fryer unit pump 152. Fryer unit pump 152 may be located either internal or external to the fryer unit 124 and is capable of discharging cooking oil to the direct line 126 so as to provide a driving force for the flow pathway of cooking oil from the fryer unit 124 to the storage receptacle 120. Such an embodiment may be in the absence of an external pumping station 132, and thus omits the necessity for the first control valve 128. According to an alternative embodiment, the storage receptacle 120 may house storage receptacle pump 154. Storage receptacle pump 154 may be located either internal or external to the storage receptacle 120 and is capable of drawing cooking oil through the direct line 126, from the fryer vat 124, and into the storage receptacle 120. Such an embodiment may be in the absence of an external pumping station 132, and thus omits the necessity for the first control valve 128. According to an alternative embodiment, the system may utilize either of the storage receptacle pump 154 or the fryer unit pump 150 in conjunction with the external pumping station 132.

When cooking oil is being transferred through the direct line 126 to the storage receptacle 120, a fryer vat oil quality sensor 156 may be placed at the outlet from the fryer vat 124. The fryer vat oil quality sensor is capable of measuring the quality of oil leaving the fryer unit 124, for example when being pumped out of the fryer unit 124 by the fryer unit pump 152. An oil quality sensor may also be placed on the fresh oil feed line 140 transferring oil from the fresh oil feed tank 122 to the fryer unit 124.

With continued reference to FIG. 12, the waste oil pumping station 132 may be equipped with a controller 720. The controller 720 may interface with any of the other units in the system, such as the storage receptacle 120, fresh oil feed tank 122, and fryer unit 124 in order to optimize the flow of cooking oil through the system, including the removal of cooking oil from the fryer unit 124.

As described above, the present disclosure has been described in association with various aspects thereof and it is understood that many changes and modifications to the described aspects can be carried out without departing from the scope and the spirit of the present disclosure that is intended to be limited only by the appended claims.

Having thus described the invention, it is now claimed:

What is claimed is:
1. A system for measuring oil quality, comprising:
 a fryer unit comprising a frying vat;
 a storage receptacle external to the fryer unit and fluidly connected to the fryer unit by plumbing configured to transfer oil from the frying vat to the storage receptacle;
 at least one oil quality sensor configured to measure the quality of oil after leaving the fryer unit and prior to entering the storage receptacle;
 a pump fluidly connected to the plumbing and configured to direct the flow of oil through the system;
 a fresh oil feed tank fluidly connected to the frying vat by a feed line; and
 a controller configured to (a) interface with any of the storage receptacle, the fryer unit, the feed tank, the pump, and the at least one oil quality sensor, (b) receive information on the quality of oil from the at least one oil quality sensor, and (c) control the flow of oil through the system;
wherein the plumbing is configured to provide for at least two paths for oil to be transferred from the frying vat to the storage receptacle, one of which does not go through the pump.

2. The system of claim 1, wherein the oil quality sensor is placed at the inlet to the storage receptacle.

3. The system of claim 1, wherein:
   the plumbing connected to the pump comprises an inlet feed and a discharge line;
   the pump is further configured to draw oil through the inlet feed and dispense oil through the discharge line; and
   the plumbing is further configured to be capable of transferring oil from the discharge line to either the storage receptacle or back into the frying vat.

4. The system of claim 3, wherein:
   the inlet feed through which oil flows into the pump is a suction wand; and
   the at least one oil quality sensor is located in said suction wand.

5. The system of claim 3, wherein the feed line is fluidly connected to the discharge line.

6. The system of claim 5, further comprising a second oil quality sensor placed downstream of the feed line's connection to the discharge line and configured to measure the quality of oil after leaving the discharge line or the feed line and prior to entering the frying vat.

7. The system of claim 3, wherein the pump is external to the fryer unit.

8. The system of claim 7, further comprising a pumping station that comprises:
   the pump; and
   the at least one oil quality sensor.

9. The system of claim 7, wherein the storage receptacle comprises a second pump in fluid communication with the plumbing.

\* \* \* \* \*